United States Patent
Hatem et al.

(10) Patent No.: US 8,372,735 B2
(45) Date of Patent: Feb. 12, 2013

(54) USJ TECHNIQUES WITH HELIUM-TREATED SUBSTRATES

(75) Inventors: Christopher Hatem, Salisbury, MA (US); Ludovic Godet, North Reading, MA (US); Alexander Kontos, Lynn, MA (US)

(73) Assignee: Varian Semiconductor Equipment Associates, Inc., Gloucester, MA (US)

( * ) Notice: Subject to any disclaimer, the term of this patent is extended or adjusted under 35 U.S.C. 154(b) by 676 days.

(21) Appl. No.: 12/339,295

(22) Filed: Dec. 19, 2008

(65) Prior Publication Data

US 2010/0041218 A1   Feb. 18, 2010

Related U.S. Application Data

(60) Provisional application No. 61/088,809, filed on Aug. 14, 2008.

(51) Int. Cl.
*H01L 21/26* (2006.01)
(52) U.S. Cl. .................. 438/513; 257/E21.334
(58) Field of Classification Search ........... 257/E21.343; 438/407, 513
See application file for complete search history.

(56) References Cited

U.S. PATENT DOCUMENTS

| | | | |
|---|---|---|---|
| 5,376,560 A | 12/1994 | Aronowitz et al. | |
| 5,585,286 A | 12/1996 | Aronowitz et al. | |
| 5,717,238 A | 2/1998 | Aronowitz et al. | |
| 5,970,353 A | 10/1999 | Sultan | |
| 6,187,643 B1 | 2/2001 | Borland | |
| 6,204,132 B1 | 3/2001 | Kittl et al. | |
| 6,225,176 B1 * | 5/2001 | Yu | 438/305 |
| 6,548,361 B1 | 4/2003 | En et al. | |
| 6,713,819 B1 | 3/2004 | En et al. | |
| 6,846,708 B2 | 1/2005 | Feudel et al. | |
| 7,361,586 B2 | 4/2008 | Adem et al. | |
| 7,410,890 B2 | 8/2008 | Kirkpatrick et al. | |
| 2008/0124858 A1 * | 5/2008 | Nguyen et al. | 438/217 |
| 2008/0124900 A1 | 5/2008 | Sasaki et al. | |

OTHER PUBLICATIONS

Sasaki, Y. et al., New Method of Plasma Doping with In-Situ Helium Pre-Amorphization, Nucl. Instr. & Meth. in Phys. Res. B 237, 2005, pp. 41-45, Elsevier.
Sasaki, Y. et al., B2H6 Plasma Doping with "In-Situ He Pre-Amorphization," 2004 Symposium on VLSI Technology, Digest of Technical Papers, 2004, pp. 180-181, Widerkehr & Associates, Gaithersburg, MD, USA.

* cited by examiner

*Primary Examiner* — Chandra Chaudhari

(57) ABSTRACT

A method of using helium to create ultra shallow junctions is disclosed. A pre-implantation amorphization using helium has significant advantages. For example, it has been shown that dopants will penetrate the substrate only to the amorphous-crystalline interface, and no further. Therefore, by properly determining the implant energy of helium, it is possible to exactly determine the junction depth. Increased doses of dopant simply reduce the substrate resistance with no effect on junction depth. Furthermore, the lateral straggle of helium is related to the implant energy and the dose rate of the helium PAI, therefore lateral diffusion can also be determined based on the implant energy and dose rate of the helium PAI. Thus, dopant may be precisely implanted beneath a sidewall spacer, or other obstruction.

9 Claims, 12 Drawing Sheets

5keV Ge PAI

12keV Ge PAI

20keV Ge PAI

Too high of energy to attain desired lateral straggle 0.5keV B

1keV B

FIG. 10A
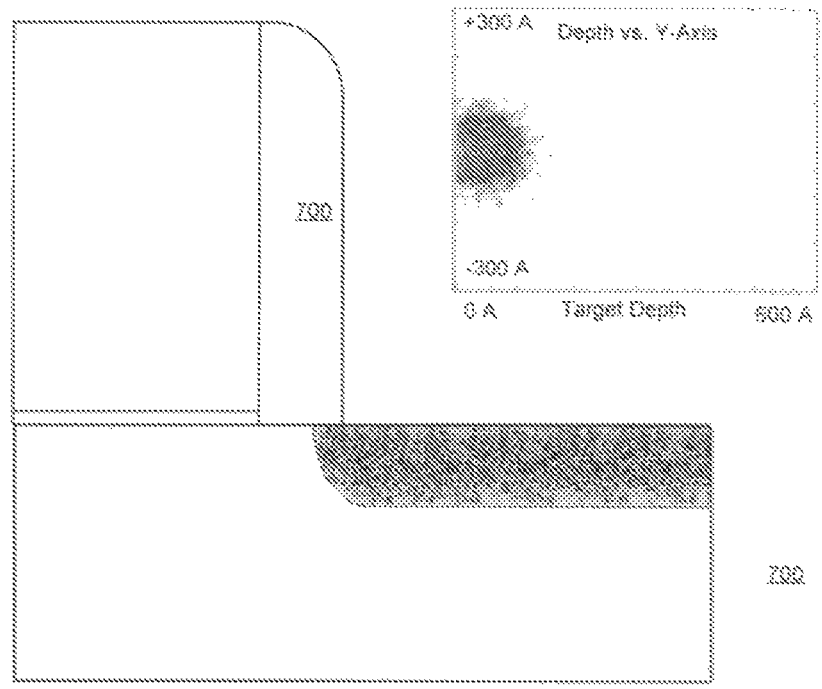
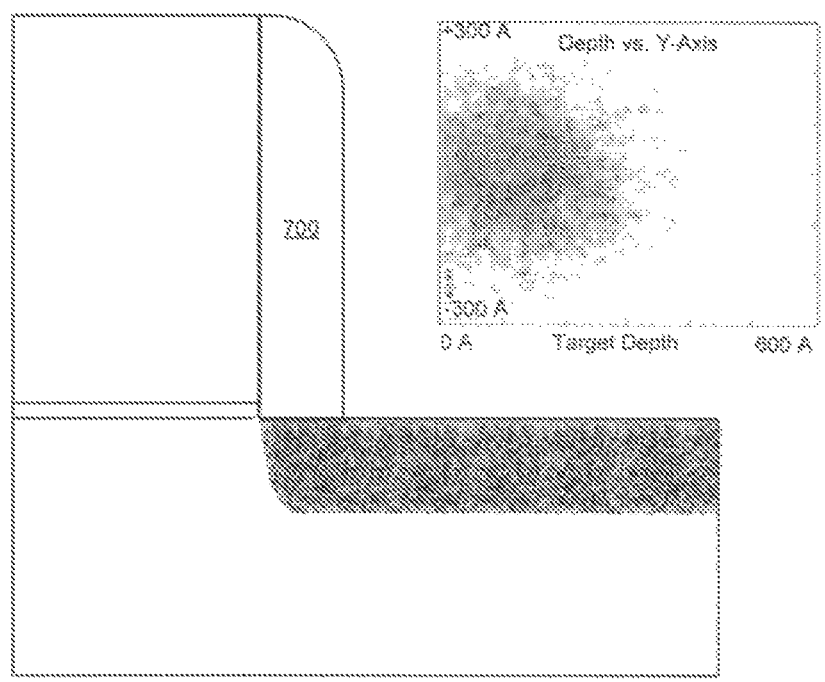
FIG. 10B

FIG. 10C
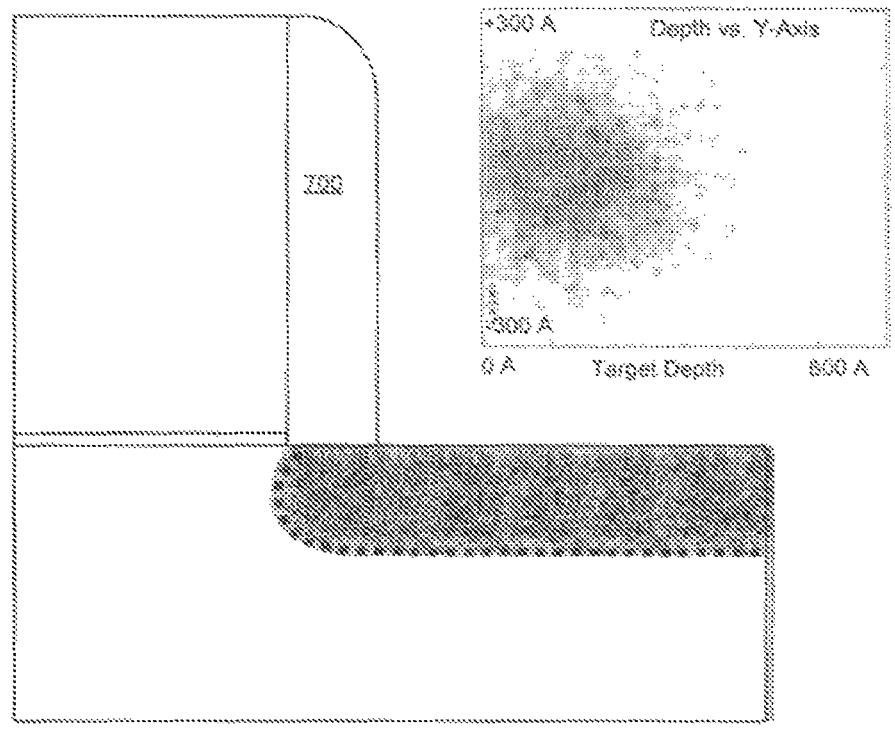
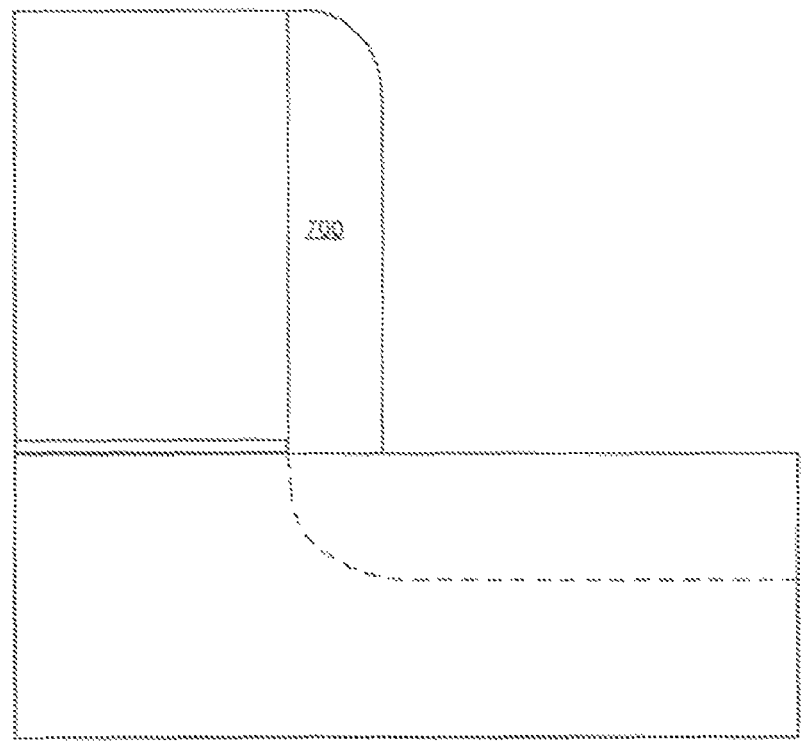
FIG. 10D

Dose Rate vs. Junction Depth (Xj)

USJ TECHNIQUES WITH HELIUM-TREATED SUBSTRATES

This application claims priority of U.S. Provisional Patent Application No. 61/088,809, filed on Aug. 14, 2008, the disclosure of which is hereby incorporated by reference.

BACKGROUND OF THE INVENTION

Ion implanters are commonly used in the production of semiconductor wafers. An ion source is used to create a beam of charged ions, which is then directed toward the wafer. As the ions strike the wafer, they impart a charge in the area of impact. This charge allows that particular region of the wafer to be properly "doped". The configuration of doped regions defines their functionality, and through the use of conductive interconnects, these wafers can be transformed into complex circuits.

FIG. 1 is a block diagram of a plasma doping system 100, while FIG. 2 is a block diagram of a beam-line ion implanter 200. Those skilled in the art will recognize that the plasma doping system 100 and the beam-line ion implanter 200 are each only one of many examples of differing plasma doping systems and beam-line ion implanters that can provide ions. This process also may be performed with other ion implantation systems or other substrate or semiconductor wafer processing equipment. While a silicon substrate is discussed in many embodiments, this process also may be applied to substrates composed of SiC, GaN, GaP, GaAs, polysilicon, Ge, quartz, or other materials known to those skilled in the art.

Turning to FIG. 1, the plasma doping system 100 includes a process chamber 102 defining an enclosed volume 103. A platen 134 may be positioned in the process chamber 102 to support a substrate 138. In one instance, the substrate 138 may be a semiconductor wafer having a disk shape, such as, in one embodiment, a 300 millimeter (mm) diameter silicon wafer. The substrate 138 may be clamped to a flat surface of the platen 134 by electrostatic or mechanical forces. In one embodiment, the platen 134 may include conductive pins (not shown) for making connection to the substrate 138.

A gas source 104 provides a dopant gas to the interior volume 103 of the process chamber 102 through the mass flow controller 106. A gas baffle 170 is positioned in the process chamber 102 to deflect the flow of gas from the gas source 104. A pressure gauge 108 measures the pressure inside the process chamber 102. A vacuum pump 112 evacuates exhausts from the process chamber 102 through an exhaust port 110 in the process chamber 102. An exhaust valve 114 controls the exhaust conductance through the exhaust port 110.

The plasma doping system 100 may further include a gas pressure controller 116 that is electrically connected to the mass flow controller 106, the pressure gauge 108, and the exhaust valve 114. The gas pressure controller 116 may be configured to maintain a desired pressure in the process chamber 102 by controlling either the exhaust conductance with the exhaust valve 114 or a process gas flow rate with the mass flow controller 106 in a feedback loop that is responsive to the pressure gauge 108.

The process chamber 102 may have a chamber top 118 that includes a first section 120 formed of a dielectric material that extends in a generally horizontal direction. The chamber top 118 also includes a second section 122 formed of a dielectric material that extends a height from the first section 120 in a generally vertical direction. The chamber top 118 further includes a lid 124 formed of an electrically and thermally conductive material that extends across the second section 122 in a horizontal direction.

The plasma doping system may further include a source 101 configured to generate a plasma 140 within the process chamber 102. The source 101 may include a RF source 150, such as a power supply, to supply RF power to either one or both of the planar antenna 126 and the helical antenna 146 to generate the plasma 140. The RF source 150 may be coupled to the antennas 126, 146 by an impedance matching network 152 that matches the output impedance of the RF source 150 to the impedance of the RF antennas 126, 146 in order to maximize the power transferred from the RF source 150 to the RF antennas 126, 146.

The plasma doping system 100 also may include a bias power supply 148 electrically coupled to the platen 134. The bias power supply 148 is configured to provide a pulsed platen signal having pulse on and off time periods to bias the platen 134, and, hence, the substrate 138, and to accelerate ions from the plasma 140 toward the substrate 138 during the pulse on time periods and not during the pulse off periods. The bias power supply 148 may be a DC or an RF power supply.

The plasma doping system 100 may further include a shield ring 194 disposed around the platen 134. As is known in the art, the shield ring 194 may be biased to improve the uniformity of implanted ion distribution near the edge of the substrate 138. One or more Faraday sensors such as an annular Faraday sensor 199 may be positioned in the shield ring 194 to sense ion beam current.

The plasma doping system 100 may further include a controller 156 and a user interface system 158. The controller 156 can be or include a general-purpose computer or network of general-purpose computers that may be programmed to perform desired input/output functions. The controller 156 can also include other electronic circuitry or components, such as application-specific integrated circuits, other hardwired or programmable electronic devices, discrete element circuits, etc. The controller 156 also may include communication devices, data storage devices, and software. For clarity of illustration, the controller 156 is illustrated as providing only an output signal to the power supplies 148, 150, and receiving input signals from the Faraday sensor 199. Those skilled in the art will recognize that the controller 156 may provide output signals to other components of the plasma doping system and receive input signals from the same. The user interface system 158 may include devices such as touch screens, keyboards, user pointing devices, displays, printers, etc. to allow a user to input commands and/or data and/or to monitor the plasma doping system via the controller 156.

In operation, the gas source 104 supplies a primary dopant gas containing a desired dopant for implantation into the substrate 138. The gas pressure controller 116 regulates the rate at which the primary dopant gas is supplied to the process chamber 102. The source 101 is configured to generate the plasma 140 within the process chamber 102. The source 101 may be controlled by the controller 156. To generate the plasma 140, the RF source 150 resonates RF currents in at least one of the RF antennas 126, 146 to produce an oscillating magnetic field. The oscillating magnetic field induces RF currents into the process chamber 102. The RF currents in the process chamber 102 excite and ionize the primary dopant gas to generate the plasma 140.

The bias power supply 148 provides a pulsed platen signal to bias the platen 134 and, hence, the substrate 138 to accelerate ions from the plasma 140 toward the substrate 138 during the pulse on periods of the pulsed platen signal. The frequency of the pulsed platen signal and/or the duty cycle of the pulses may be selected to provide a desired dose rate. The amplitude of the pulsed platen signal may be selected to provide a desired energy. With all other parameters being equal, a greater energy will result in a greater implanted depth. The plasma doping system 100 may incorporate hot or cold implantation of ions in some embodiments.

Turning to FIG. 2, a beam-line ion implanter 200 may produce ions for treating a selected substrate. In one instance, this may be for doping a semiconductor wafer. In general, the beam-line ion implanter 200 includes an ion source 280 to generate ions that form an ion beam 281. The ion source 280 may include an ion chamber 283 and a gas box containing a gas to be ionized. The gas is supplied to the ion chamber 283 where the gas is ionized. This gas may be or may include or contain, in some embodiments, hydrogen, helium, other rare gases, oxygen, nitrogen, arsenic, boron, phosphorus, carborane, alkanes, or another large molecular compound. The ions thus generated are extracted from the ion chamber 283 to form the ion beam 281. A power supply is connected to an extraction electrode of the ion source 280 and provides an adjustable voltage.

The ion beam 281 passes through a suppression electrode 284 and ground electrode 285 to mass analyzer 286. Mass analyzer 286 includes resolving magnet 282 and masking electrode 288 having resolving aperture 289. Resolving magnet 282 deflects ions in the ion beam 281 such that ions of a desired ion species pass through the resolving aperture 289. Undesired ion species do not pass through the resolving aperture 289, but are blocked by the masking electrode 288.

Ions of the desired ion species pass through the resolving aperture 289 to the angle corrector magnet 294. Angle corrector magnet 294 deflects ions of the desired ion species and converts the ion beam from a diverging ion beam to ribbon ion beam 212, which has substantially parallel ion trajectories. The beam-line ion implanter 200 may further include acceleration or deceleration units in some embodiments.

An end station 211 supports one or more substrates, such as substrate 138, in the path of ribbon ion beam 212 such that ions of the desired species are implanted into substrate 138. The substrate 138 may be, for example, a silicon wafer or a solar panel. The end station 211 may include a platen 295 to support the substrate 138. The end station 211 also may include a scanner (not shown) for moving the substrate 138 perpendicular to the long dimension of the ribbon ion beam 212 cross-section, thereby distributing ions over the entire surface of substrate 138. Although the ribbon ion beam 212 is illustrated, other embodiments may provide a spot beam.

The ion implanter 200 may include additional components known to those skilled in the art. For example, the end station 211 typically includes automated substrate handling equipment for introducing substrates into the beam-line ion implanter 200 and for removing substrates after ion implantation. The end station 211 also may include a dose measuring system, an electron flood gun, or other known components. It will be understood to those skilled in the art that the entire path traversed by the ion beam is evacuated during ion implantation. The beam-line ion implanter 200 may incorporate hot or cold implantation of ions in some embodiments.

As stated above, ion implantation is a standard technique for introducing conductivity-altering impurities into semiconductor substrates. A desired impurity material is ionized in an ion source, the ions are accelerated, and the ions are directed at the surface of the substrate. The energetic ions penetrate into the bulk of the semiconductor material. Following an annealing process, the ions may become incorporated into the crystalline lattice of the semiconductor material to form a region of desired conductivity.

Silicon or other materials may also have an amorphous crystal structure. In a silicon substrate, one silicon atom is usually tetrahedrally bonded to four neighboring silicon atoms and these silicon atoms will form a well-ordered lattice across the substrate. In contrast, this order does not exist in amorphous silicon. Instead, the silicon atoms form a random network and the silicon atoms may not be tetrahedrally bonded to four other silicon atoms. In fact, some silicon atoms may have dangling bonds.

Amorphizing implants, such as a pre-amorphizing implant (PAI), are used to amorphize the crystal lattice of a substrate. Prior to the amorphizing implant, the substrate usually has a crystal lattice with a long-range order. Such a structure allows implanted ions to move through the crystal, or channel. By amorphizing the substrate, channeling of dopants, or implantation of ions substantially between the crystal lattice of the substrate, during later implantation may be prevented or reduced because the substrate will lack a long-range order. Thus, the dopant implant profile may be kept shallow.

Previously, USJ formation had been performed with a PAI using heavier species such as germanium and silicon to prevent channeling. This method may cause residual damage at the end of range and subsequent leakage in complementary metal oxide semiconductor (CMOS) transistors. Yet, if the PAI step was removed, channeling of ions will occur, thereby increasing the junction depths. Additionally, advances in USJ have required annealing technologies capable of millisecond (MS) thermal budgets near a target temperature. A MS anneal is unable to completely remove implant damage caused by silicon or germanium PAI, and specifically end of range (EOR) defects. Furthermore, there is a lack of lateral diffusion of a dopant in the substrate. This lack of lateral diffusion may cause overlap capacitance issues within a device.

Accordingly, there is a need to improve the implantation methods used to form USJ and, more particularly, there is a need to create methods using helium to form ultra shallow junctions.

SUMMARY OF THE INVENTION

The problems of the prior art are addressed by the present disclosure, which describes a method of using helium to create ultra shallow junctions. A pre-implantation amorphization using helium has significant advantages. For example, it has been shown that upon anneal dopants will penetrate the substrate only to the original amorphous-crystalline interface, and no further. Therefore, by properly determining the implant energy of helium, it is possible to exactly determine the junction depth. Increased doses of dopant enhance the activation thereby lowering the substrate resistance without affecting junction depth. Furthermore, the lateral straggle of helium is related to the implant energy and the dose rate of the helium PAI, therefore lateral diffusion can also be determined based on the implant energy and dose rate of the helium PAI. Thus, dopant may be precisely implanted beneath a sidewall spacer, or other obstruction.

BRIEF DESCRIPTION OF THE DRAWINGS

For a better understanding of the present disclosure, reference is made to the accompanying drawings, in which like elements are referenced with like numerals, and in which:

FIGS. 10A-10D are cross-sectional views of improving lateral straggle; and

DETAILED DESCRIPTION OF THE INVENTION

Figure 3:
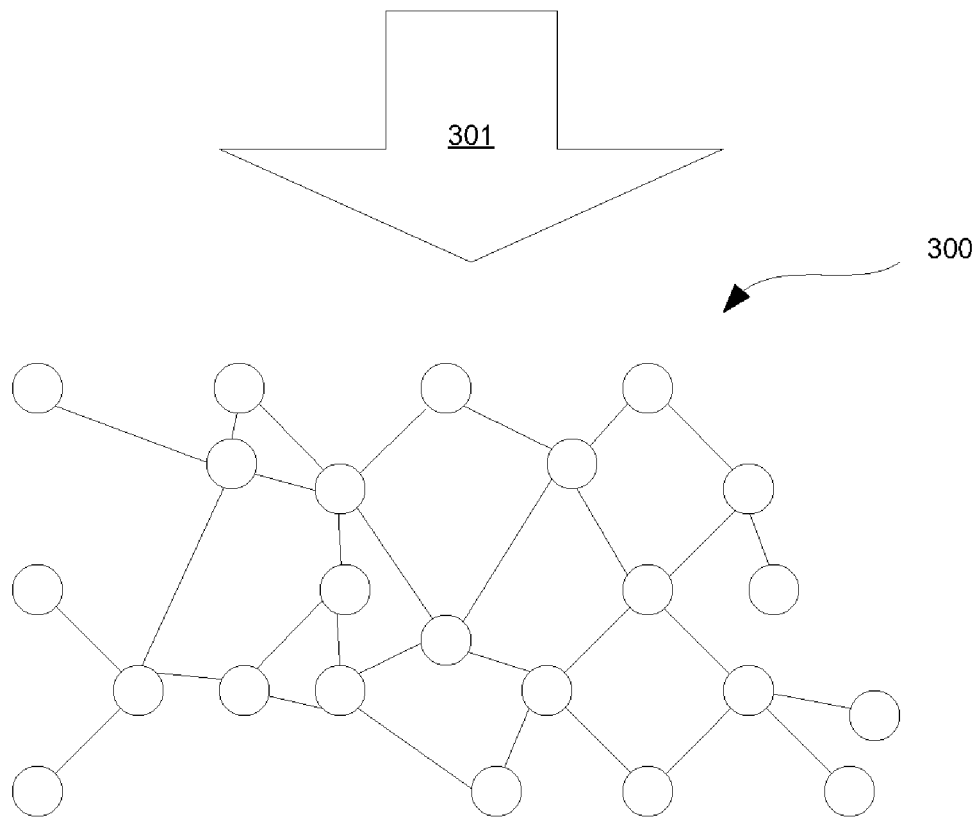
FIG. 3 is a substrate with an amorphous crystal structure caused by a PAI.

As stated above, silicon is typically a crystalline structure, where each silicon atom is tetrahedrally bonded to four neighboring silicon atoms. By bombarding this crystalline structure with atoms, such as silicon, germanium, or helium, the crystalline structure of the silicon workpiece can be altered. FIG. 3 is a substrate with an amorphous crystal structure. This crystal lattice 300 is implanted with ions 301 to cause this amorphous structure. This crystal lattice 300 which may be made up of, for example, silicon atoms, is amorphous, lacks a long-range order, and includes some atoms with dangling bonds. These ions 301 may be part of a helium PAI, for example. Since the crystal lattice 300 lacks a long-range order, the channels within the crystal lattice 300 do not exist. Thus, ions are unable to channel between the crystal lattice 300.

By bombarding ion to amorphize the substrate, channeling of implanted ions can be eliminated. However, while PAI eliminates the channeling issue, it causes other problems. The implantation of ions, specifically heavier species such as germanium and silicon, causes residual damage at end of range (EOR). The end of range is the lowest depth within the substrate where implanted ions reach. These EOR defects cause subsequent leakage in the CMOS transistors. Ultra shallow junctions also require annealing techniques capable of millisecond (MS) thermal budgets near the target temperature. Two drawbacks in the MS only anneal are the inability to completely remove the implant damage, specifically EOR defects described above, and the lack of lateral diffusion of the dopant, which causes overlap capacitance issues within the device.

A helium PAI solves the problems of preventing channeling of ions and enabling a MS anneal. As is the case with other implants, a helium PAI has the ability to amorphize a substrate so that channeling of ions is prevented. In addition, it has been found that a helium PAI also results in no residual damage after annealing. Additionally, during the anneal process after a helium PAI, some implanted dopant ions, such as boron, carborane, arsenic, phosphorus and others, will transport to the original amorphous-crystalline interface that was created by the helium PAI. Tests have shown that these implanted ions do not diffuse past the original amorphous-crystalline interface, rather they stop at that interface. This transport phenomenon gives helium the ability to tailor junction depth ($x_j$) and/or lateral diffusion. A helium PAI may, thus, enable an MS anneal by overcoming issues associated with lateral diffusion. The helium PAI also may enable an MS anneal or tailoring of junction depth for other dopants besides boron, such as arsenic or phosphorus. A helium PAI also will fully repair with a solid phase epitaxy (SPE) anneal or MS anneal whereas a germanium or silicon PAI will not. Furthermore, because there is no residual damage, a helium PAI also will not cause substantial leakage, unlike a germanium PAI.

Figure 4A:
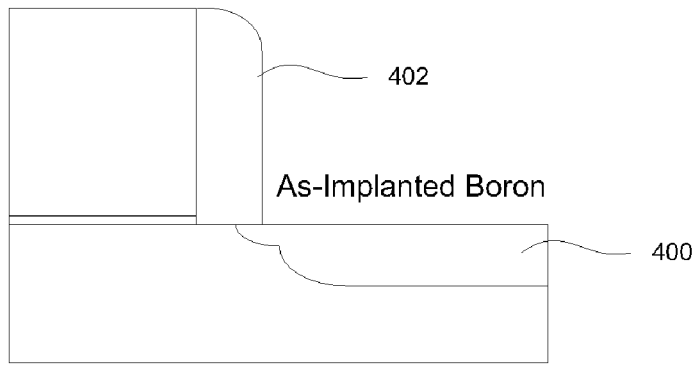
FIGS. 4A-4C are cross-sectional views of actual versus target profiles.
Figure 4B:
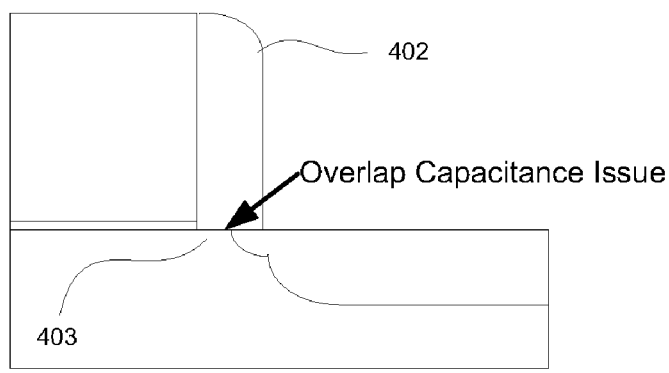
Figure 4C:
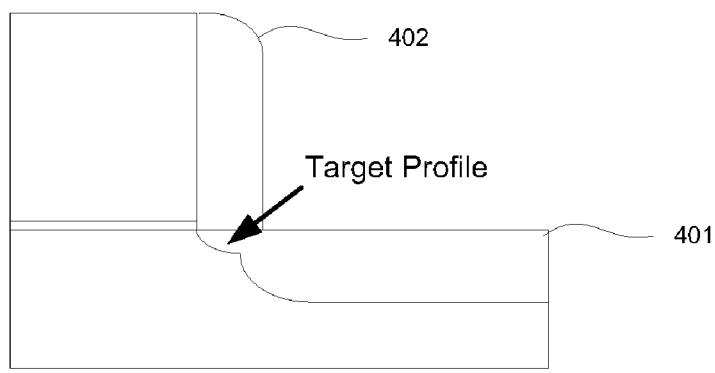

As mentioned above, use of an MS anneal without a rapid thermal processing (RTP) step for germanium or silicon PAI has two main issues. First, there is an inability to fully repair implant damage, which may lead to device leakage. Second, there is a lack of lateral diffusion. Lateral diffusion is the diffusion of a dopant, such as boron, from the implanted region to the target profile after anneal. This is problematic; especially in the region beneath the sidewall spacers. FIGS. 4A-4C are cross-sectional views of actual profiles versus target profiles. FIG. 4C shows the target profile 401, where boron is implanted beneath the sidewalls 402. FIG. 4A shows the actual implanted region 400 following a MS anneal. The lack of lateral diffusion keeps the actual profile 400 from achieving the target profile 401, leaving a gap between the gate and the implanted region, as shown in FIG. 4B. This may lead to overlap capacitance issues or undesired channel conductance.

Figure 11A:
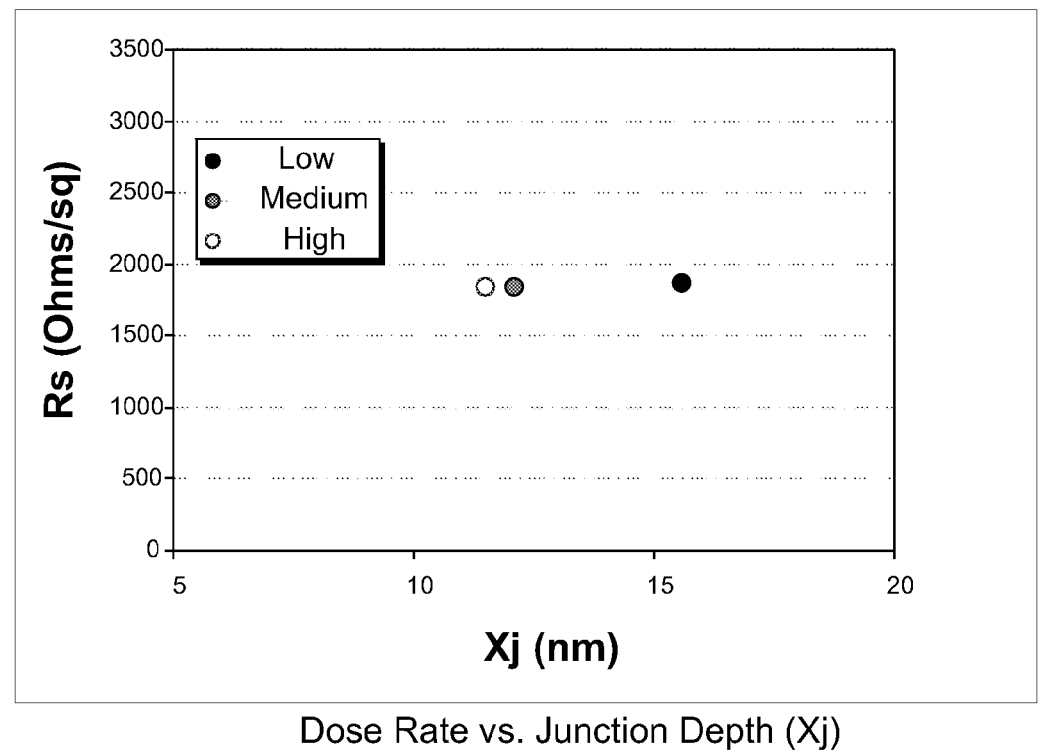
FIGS. 11A-11B illustrate junction depth using helium PAI.
Figure 11B:
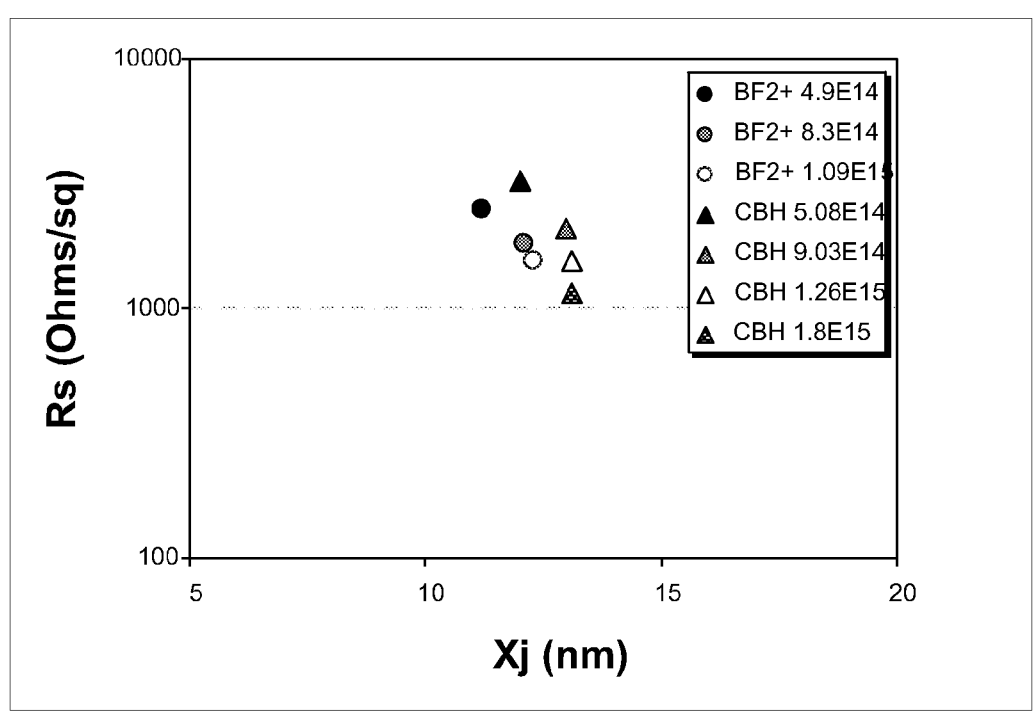

FIGS. 11A-11B show several important characteristics of helium PAI. In FIG. 11A, the dose rate of the helium is varied, while the Rs is kept constant. The graph shows that by varying the helium dose rate, a predefined junction depth can be achieved for a specific substrate resistance. Higher dose rates result in shallower junction depths.

FIG. 11B shows the effects of increased dopant dose on a substrate which has undergone helium PAI. Note that in this case, the dose of a particular dopant does not affect the junction depth, rather only the Rs is changed. In other words, increasing doses of dopant retain the same junction depth, but with a reduction in substrate resistance. In all cases, a fixed helium PAI of a predetermined dose rate and implant energy was performed. Following that, ion implants of $BF_2$ and carborane were performed at various doses, and the resulting junction depths were measured. Note that in the case of carborane, the increased dose does not increase the junction depth beyond about 13 nm. While the graph shows an increase in junction depth resulting from an increased dose of $BF_2$, it is believed that the dopant has not yet reached the amorphous-crystalline interface. Further increases in the dose of BF2 would show similar results to those demonstrates by carborane. Thus, junction depth can be determined by proper dose rate during the helium PAI.

Figure 5:
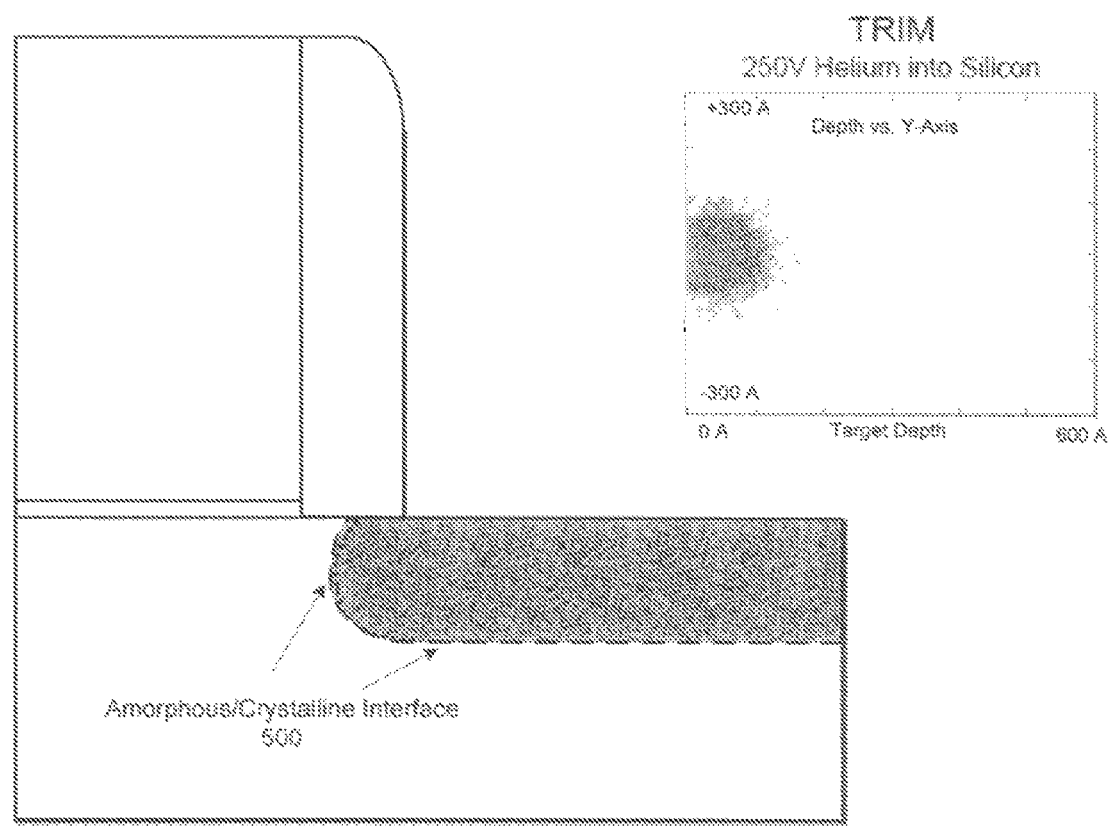
FIG. 5 is a cross-sectional view of the amorphous-crystalline interface.

FIG. 5 is a cross-sectional view of semiconductor substrate following a helium PAI. The depth of the helium atoms defines the amorphous-crystalline interface 500. As shown in FIG. 11B, subsequent implants will diffuse only to the amorphous-crystalline interface, and no further. In other words, the dopants will diffuse through the amorphous region, but may not diffuse into the crystalline region. Thus, the shape and depth of the dopant profile may be tailored by the proper application of the helium PAI. In some embodiments, the implant energy of the helium PAI is varied to determine the thickness of the amorphous layer. In a plasma processing system, implant energy is controlled by the magnitude of the bias voltage applied to the platen. In a beamline system, implant energy can be controlled by the voltage applied to the electrodes 284, 285. In another embodiment, the thickness of the amorphous layer may be controlled by using a constant energy during the PAI implant. For example, as shown in FIG. 11A, the dose rate of the helium PAI can control the depth of amorphous layer. In a plasma processing system, the dose rate can be changed by varying the RF power as controlled by antenna 126, 146, implant pressure, the duty cycle of the platen bias voltage, or He flow. In a beam line system, dose rate can be varied by varying the extracted ion beam current, or by modifying the size or shape of the ion beam.

Figure 6:
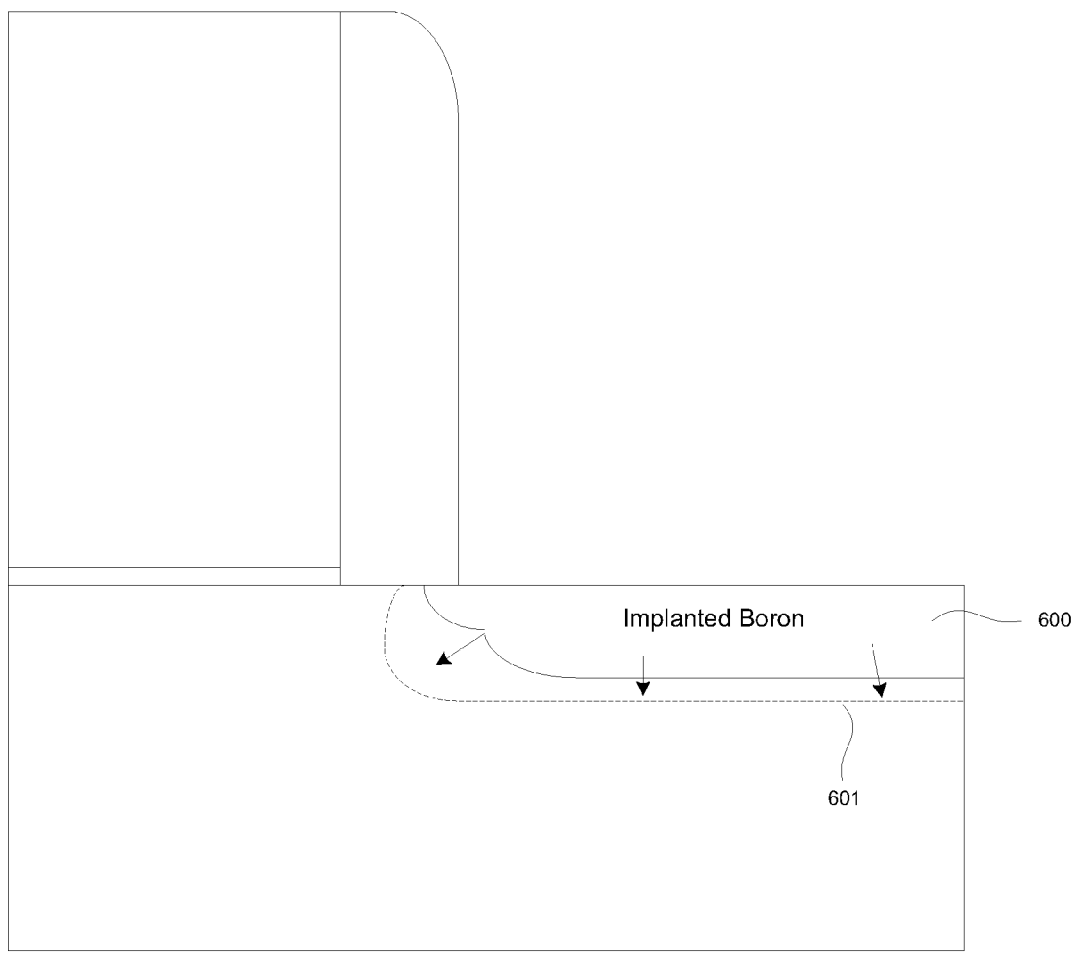
FIG. 6 is a cross-sectional view of boron diffusion.

FIG. 6 is a cross-sectional view of a substrate following a boron diffusion occurring after a helium PAI. If boron is implanted in only the implanted region 600, the boron will diffuse throughout the amorphized region caused by a PAI implant that is within the amorphous-crystalline interface (represented by the dotted line 601 in FIG. 6). The boron will not substantially diffuse past the amorphous-crystalline interface. In one particular embodiment, the helium PAI is implanted at 250V in the plasma doping system 100, although other bias voltages or implantation methods are possible.

Figure 7:
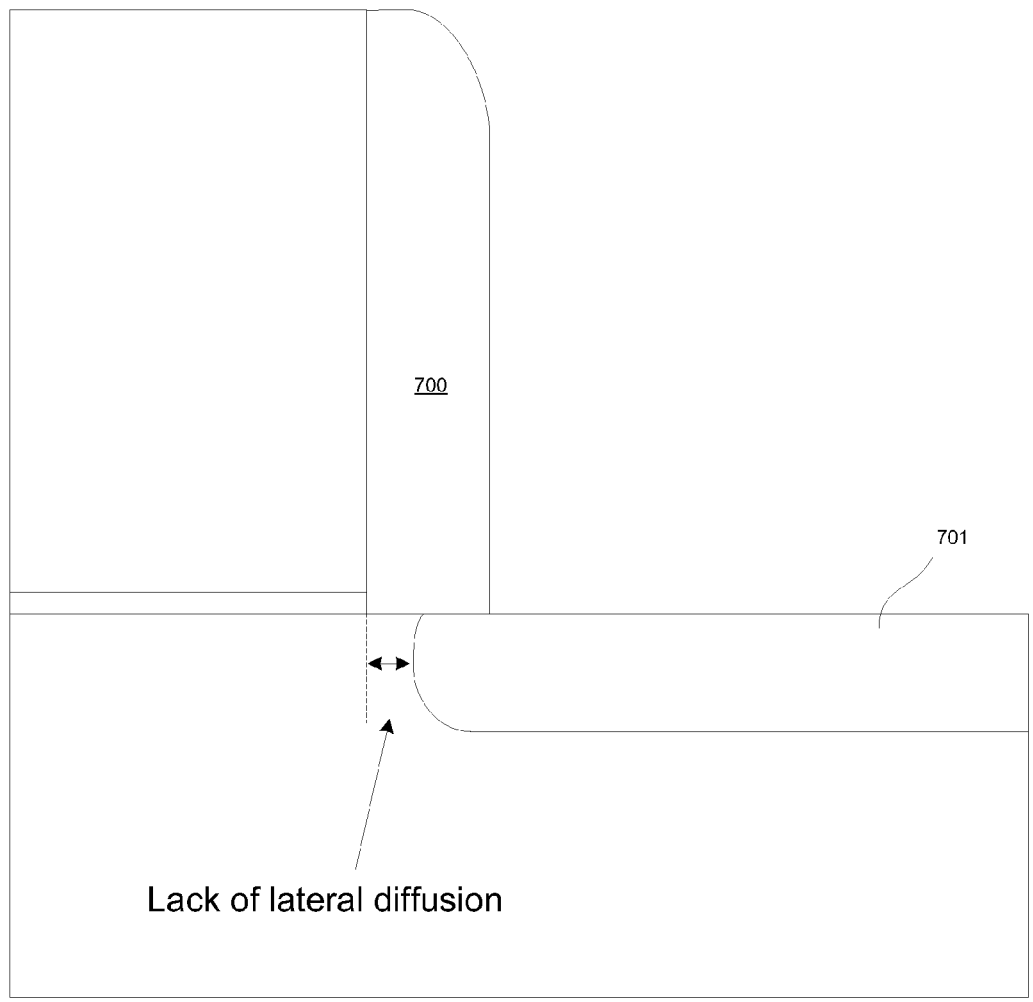
FIG. 7 is a cross-sectional view of a lack of lateral diffusion.

Notice that the helium PAI shown in FIGS. 5 and 6 create an amorphous-crystalline interface that is located beneath the sidewall spacer 700. However, this amorphous-crystalline interface does not extend to the gate. FIG. 7 is a cross-sectional view of the semiconductor device, which demonstrates this lack of lateral diffusion. This lack of lateral diffusion may lead to overlap capacitance, as shown in FIG. 4. Since the dopant cannot diffuse past the amorphous-crystalline interface, improper placement of an amorphous-crystalline interface may at least partly cause this lack of lateral diffusion. To avoid overlap capacitance, the implanted dopant 701 needs to diffuse fully under the sidewall spacer 700. In order for this to occur, the amorphous-crystalline interface must be located near the gate.

One factor that affects the location of the amorphous-crystalline interface in FIGS. 5-7 is the lateral straggle of helium during the PAI process. Lateral straggle is defined as the motion of ions parallel to the wafer as a result of ion implantation. In other words, more lateral movement (or straggle) would create an amorphous-crystalline interface that extends further beneath the sidewall spacer.

Figure 1:
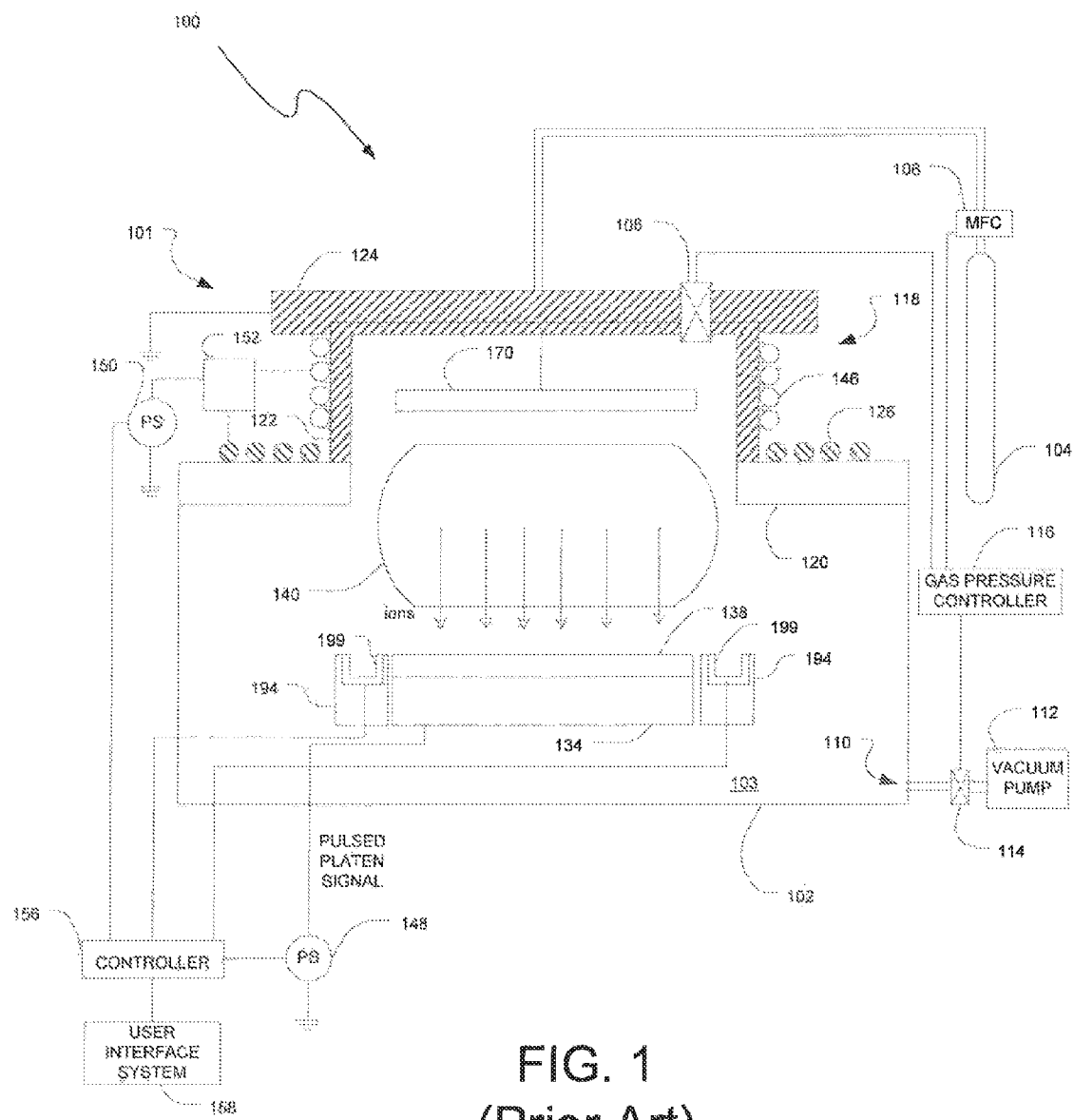
FIG. 1 is a block diagram of a plasma doping system.
Figure 2:
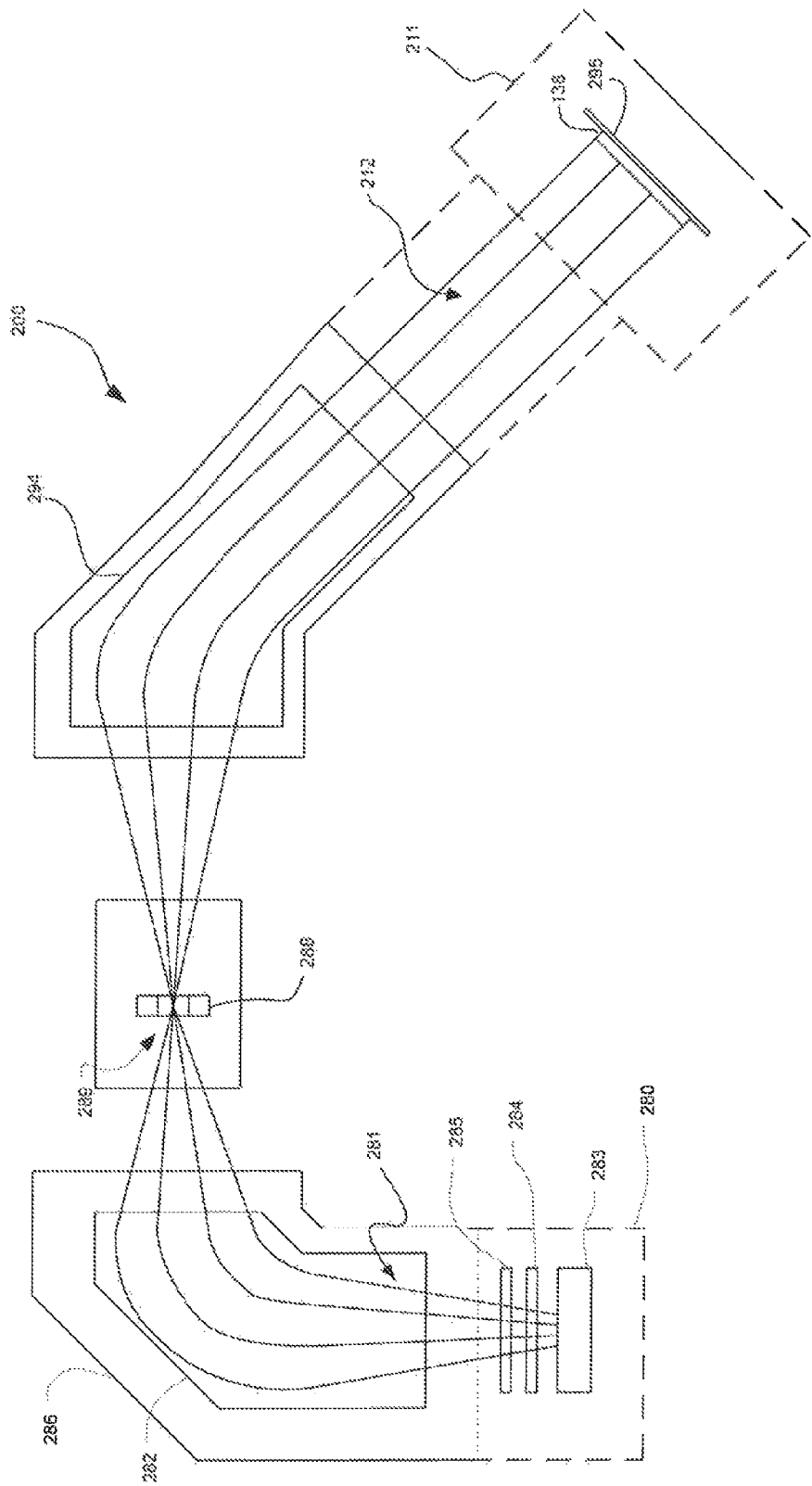
FIG. 2 is a block diagram of a beam-line ion implanter.
Figures 8A, 8B, 8C:
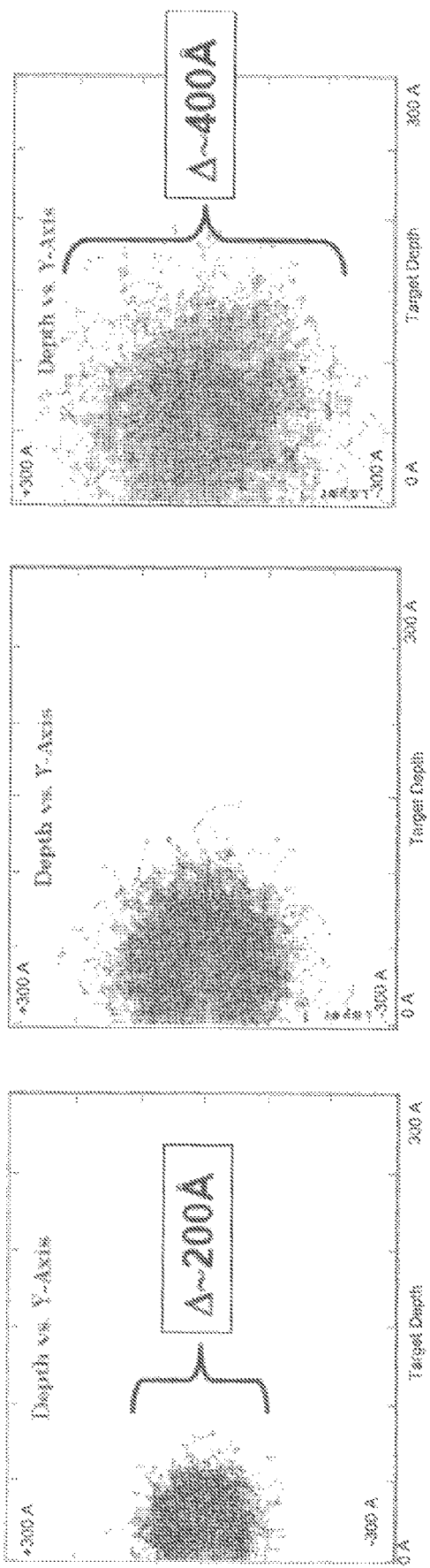
FIGS. 8A-8C illustrate lateral straggle control.

FIGS. 8A-8C illustrate the use of implant voltage to control lateral straggle. Use of an atom with a light atomic weight, such as helium, and varied implant energy allows control of this lateral straggle. Control of lateral straggle allows control of lateral amorphization and, therefore, dopant lateral diffusion. FIGS. 8A-8C illustrate the effect of increased implant energy. In all cases, a helium PAI was performed using a plasma doping system 100, as shown in FIG. 1, followed by a boron ion implantation. FIG. 8A shows the profile of dopant within the substrate when the helium implanted at a voltage of 250V. Note that the diffusion profile has a depth of roughly 150 Å, while the implanted ions have a lateral straggle of about 200 Å. Increasing the voltage applied to the platen to 500V during PAI, as shown in FIG. 8B, creates a larger diffusion profile, about 200 Å in depth and 300 Å in the lateral direction. Finally, applying a voltage of about 1000V to the platen during the helium PAI creates a diffusion profile having a depth of about 300 Å and dispersion of about 400 Å in the lateral direction. Thus, by modifying the implant energy of the helium PAI, the region of dopant diffusion may be changed and lateral straggle may be controlled. Similar result may be achieved using a beam line system by modifying the voltage applied to the extraction electrodes.

Figure 9A:
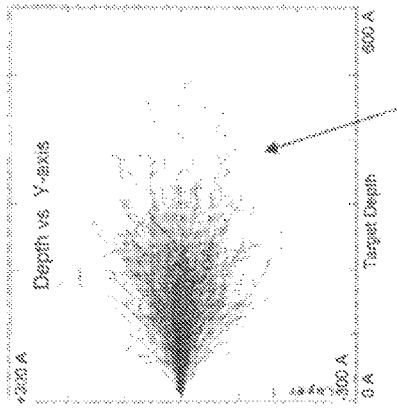
FIGS. 9A-9E illustrate lateral straggle control.
Figure 9B:
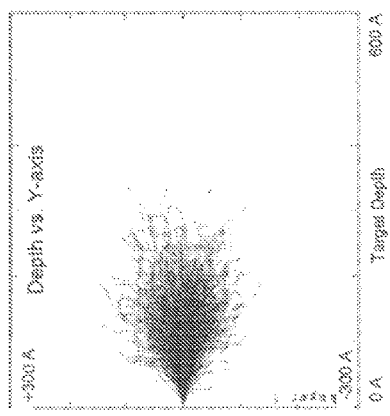
Figure 9C:
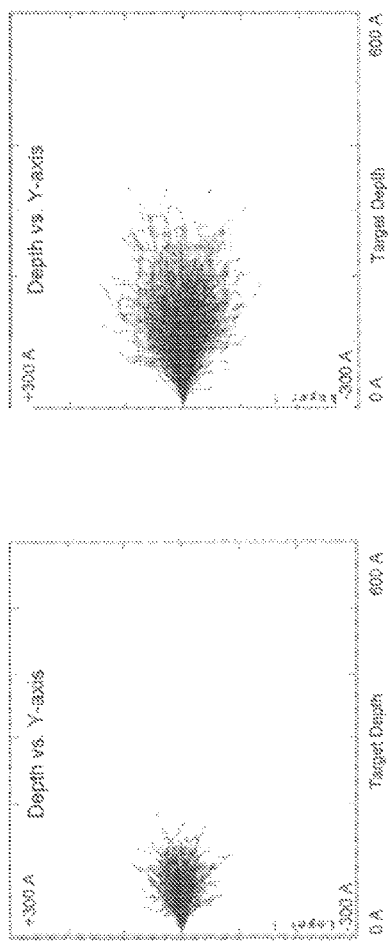
Figure 9D:
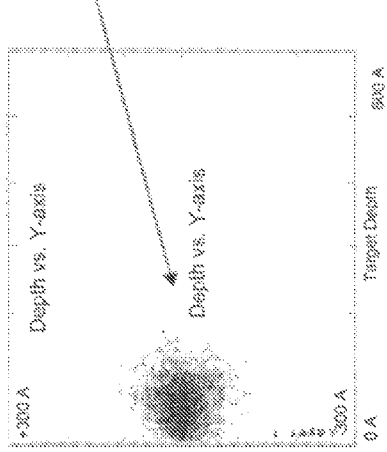
Figure 9E:
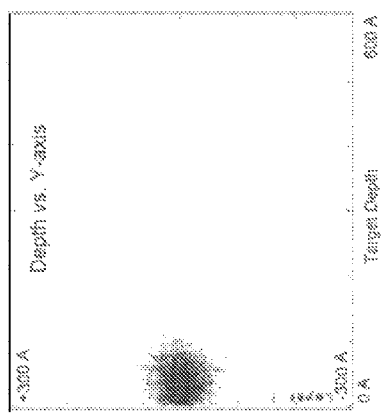

FIGS. 9A-9E illustrate lateral straggle control when germanium is used to perform the PAI. A germanium PAI is illustrated in FIGS. 9A-9C and a boron PAI is illustrated in FIGS. 9D-9E. At higher energies, as shown in FIGS. 9B-9C, the germanium PAI does not allow lateral straggle to be controlled. This is because germanium is much heavier than helium and thus, implants deep into the substrate rather than dispersing quickly like a helium PAI. Note that even at 20 KeV, germanium does not have the lateral straggle seen in helium at much lower energy levels. FIGS. 9D-9E show that boron, which is lighter than germanium, does not penetrate as deeply as germanium. However, the increased implant energy does little to affect the lateral straggle, while it does increase the junction depth.

FIGS. 10A-10D are cross-sectional views of a semiconductor device showing the method used to improve lateral straggle. In FIG. 10A, a 250V He PAI is performed, as was described with respect to FIG. 8A. However, this energy level does not result in enough lateral straggle because the amorphous-crystalline interface is not fully under the sidewall spacer 700. Thus, the dopant likely would not fully diffuse under the sidewall spacer and overlap capacitance could occur. A higher implant energy, such as 1000V is illustrated in FIG. 10B and shows improved lateral straggle. The boron in this instance will diffuse to the amorphous-crystalline interface represented by the dotted line of FIG. 10C. This He PAI will result in the ideal dopant profile shown in FIG. 10D with either an MS anneal or an SPE anneal.

Use of a helium PAI may prevent channeling of a subsequent implant followed by a low-angle source drain extension (SDE) implant. Thus, the dopant may be placed at least partly under any sidewall spacers. The helium PAI also may overcome any problems with lateral diffusion that are caused by a MS anneal or SPE anneal. In the plasma doping system 100, ramp voltage, pressure, or other parameters may be configured to control lateral diffusion.

Variations in the implant voltage of the helium PAI may increase lateral straggle and, consequently, lateral amorphization under the sidewall spacer, or any other obstruction, such as photomask material. Boron, carborane, arsenic, phosphorus or other implanted ions, will diffuse to this amorphous-crystalline interface at the desired location during an anneal to achieve an optimal active dopant profile. Furthermore, the implant energy and the dose rate of the helium PAI may be configured to adjust the amorphous-crystalline interface that determines the implanted ion junction depth during an anneal. The ability of helium to stop boron diffusion at this interface may allow tailoring of a USJ.

An embodiment of the method described herein is not solely limited to placing a dopant under a sidewall spacer. Rather, it may be applied to other doping methods. For example, applications where precise junction depth or extensive or precise lateral diffusion is required may benefit from an embodiment of the process described herein. By varying the implant energy and the dose rate of the helium PAI, both the lateral straggle and the junction depth can be controlled.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method of implanting ions in a workpiece, said ions creating an implanted region having a specific junction depth and extending beneath an obstruction, comprising:
    determining a width of said obstruction;

determining an implant voltage and dose rate needed to a lateral straggle equal to said width while maintaining said specific junction depth;

performing a helium pre-amorphizing implant (PAI) at said implant voltage and said dose rate; and implanting ions, following said helium PAI, which diffuse under said obstruction to said specific junction depth.

2. The method of claim 1, wherein said obstruction comprises a sidewall.

3. The method of claim 1, wherein said obstruction comprises a photomask.

4. The method of claim 1, wherein said helium PAI and said implanting are performed using a plasma processing system.

5. The method of claim 4, wherein said plasma processing system comprises a platen on which said workpiece is placed and wherein said implant voltage is determined by a bias voltage applied to said platen.

6. The method of claim 4, wherein said plasma processing system comprises an antenna to create a plasma, and said dose rate is determined based on a power supplied to said antenna.

7. The method of claim 4, wherein said plasma processing system comprises a platen on which said workpiece is placed and wherein said dose rate is determined by a duty cycle of a bias voltage applied to said platen.

8. The method of claim 1, wherein said helium PAI and said implanting are performed using a beamline system.

9. The method of claim 8, wherein said buntline system comprises a ion source and at least one extraction electrode, and wherein said implant voltage is determined by a voltage applied to said extraction electrode.

* * * * *

UNITED STATES PATENT AND TRADEMARK OFFICE
CERTIFICATE OF CORRECTION

PATENT NO. : 8,372,735 B2  
APPLICATION NO. : 12/339295  
DATED : February 12, 2013  
INVENTOR(S) : Hatem et al.

It is certified that error appears in the above-identified patent and that said Letters Patent is hereby corrected as shown below:

In the Claims

Column 10, claim 9, line 10, "said buntline system" should appear as "said beamline system"

Signed and Sealed this
Twenty-third Day of April, 2013

Teresa Stanek Rea
*Acting Director of the United States Patent and Trademark Office*